United States Patent [19]
Chu et al.

[11] Patent Number: 5,683,985
[45] Date of Patent: Nov. 4, 1997

[54] OLIGONUCLEOTIDE DECOYS AND METHODS RELATING THERETO

[75] Inventors: Barbara Chen Fei Chu, Del Mar; Leslie Orgel, La Jolla, both of Calif.

[73] Assignee: The Salk Institute for Biological Studies, La Jolla, Calif.

[21] Appl. No.: 122,433

[22] PCT Filed: Apr. 17, 1992

[86] PCT No.: PCT/US92/03205

§ 371 Date: Sep. 22, 1993

§ 102(e) Date: Sep. 22, 1993

Related U.S. Application Data

[63] Continuation-in-part of Ser. No. 687,337, Apr. 18, 1991, abandoned.

[51] Int. Cl.⁶ .................................................. A61K 48/00
[52] U.S. Cl. ...................... 514/44; 435/69.1; 435/172.3; 436/501; 536/23.1; 536/24.1; 536/24.3; 536/24.31; 536/24.32; 536/24.33
[58] Field of Search .................... 435/6, 69.1, 172.3; 536/501, 22.1, 23.1, 24.1, 24.3–24.33; 514/44

[56] References Cited

U.S. PATENT DOCUMENTS 4,582,789  4/1986  Sheldon, III et al. ...................... 435/6

FOREIGN PATENT DOCUMENTS

| | | |
|---|---|---|
| 0 292 802 A2 | 11/1988 | European Pat. Off. . |
| 0 292 802 A3 | 11/1988 | European Pat. Off. . |
| 0 427 073 A2 | 5/1991 | European Pat. Off. . |
| 0 427 074 A2 | 5/1991 | European Pat. Off. . |
| 0 572 287 A2 | 12/1993 | European Pat. Off. . |
| WO 90/00626 | 1/1990 | WIPO . |
| WO 90/03445 | 4/1990 | WIPO . |
| WO 90/11322 | 10/1990 | WIPO . |
| WO 92/19732 | 11/1992 | WIPO . |

OTHER PUBLICATIONS

Bielinska et al., "Regulation of Gene Expression with Double–Stranded Phosphorothioate Oligonucleotides" *Science* 250:997–1000 (1990).

Clusel et al., "Ex vivo regulation of specific gene expression by nanomolar concentration of double–stranded dumbell oligonucleotides" *Nucleic Acids Research* 21(15) 3405–3411 (1993).

Erie et al., "A Dumbbell–Shaped, Double–Hairpin Structure of DNA: A Theromodynamic Investigation" *Biochemistry* 26(22):7150–7159 (1987).

Marky et al., "Loop formation in polynucleotide chains. I. Theory of hairpin loop closure" *Chemical Abstracts* Abstract No. 48885t, vol. 98(7), p. 265, col. 1 (1983).

Sriprakash et al., "Hairpin extension: a general method for the improvement of sensitivity of oligonucleotide probes" *Chemical Abstracts* Abstract No. 18772y, vol. 111(3), p. 176, col. 2 (1989).

van de Sande et al., "Parallel Stranded DNA" *Science* 241:551–557 (1988).

Chu et al. (1989) Nucleic Acids Research, vol. 17, No. 12, pp. 4783–4798.

*Primary Examiner*—Ardin H. Marschel
*Attorney, Agent, or Firm*—Gary Cary Ware & Freidenrich; Stephen E. Reiter

[57] ABSTRACT

Improved DNA structures are disclosed which contain target sequences which bind to control proteins (such as the CREB protein). The structures of the present invention are stable to degradation, and are effective as decoys for control proteins, making it possible to modulate the transcriptional control normally exerted by such control proteins. In addition, there is provided a method to reversibly crosslink oligonucleotides to polypeptides which recognize the oligonucleotide sequence. This method involves synthesizing DNA structures as described above, wherein one or more phosphorothioate diester linkages are incorporated into the resulting oligonucleotide, allowing the phosphorothioate diester-containing oligonucleotide to bind to polypeptides which recognize the sequence of said oligonucleotide, then contacting the polypeptide-bound oligonucleotide with a transition metal reagent.

20 Claims, 2 Drawing Sheets

$n \geq 1$ n ≥ 1

5,683,985

SEQUENCE LISTING ( 1 ) GENERAL INFORMATION:

( i i i ) NUMBER OF SEQUENCES: 47

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:1:

AAATTGACGT CATGGTAA                                                18

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:2:

TTACCATGAC GTCAATTT                                                18

( 2 ) INFORMATION FOR SEQ ID NO:3:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:3:

AAATTGACGT CATGGTAACT CTCTTACCAT GACGTCAATT T                                41

( 2 ) INFORMATION FOR SEQ ID NO:4:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:4:

GTAACTCTCT TACCATGACG TCAATTTCTC TCAAATTGAC GTCATG                            46

( 2 ) INFORMATION FOR SEQ ID NO:5:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: circular ( i i ) MOLECULE TYPE: other nucleic acid ( x i ) SEQUENCE DESCRIPTION: SEQ ID NO:5:

GTAACTCTCT TACCATGACG TCAATTTCTC TCAAATTGAC GTCATG                            46

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: other nucleic acid ( x i ) SEQUENCE DESCRIPTION: SEQ ID NO:6:

AAATTTACAT ATTACACATA T                                                      21

( 2 ) INFORMATION FOR SEQ ID NO:7:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:7:

AAATTTACAT ATTACACATA TTCTCTATAT GTGTAATATG TAAATTT                           47

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: double
        ( D ) TOPOLOGY: linear ( i i ) MOLECULE TYPE: other nucleic acid ( x i ) SEQUENCE DESCRIPTION: SEQ ID NO:8:

AGGGACTTTC CGCTGGGGAC TTTTC                                                  25

( 2 ) INFORMATION FOR SEQ ID NO:9:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:9:

```
AGGGACTTTC CGCTGGGGAC TTTTCTTTTT GAAAAGTCCC CAGCGGAAAG TCCCT        55
```

( 2 ) INFORMATION FOR SEQ ID NO:10:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:10:

```
ACTCTCTGTG TCTGACTCAT GCTCTCTCAG CATGAGTCAG ACAC        44
```

( 2 ) INFORMATION FOR SEQ ID NO:11:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: circular ( i i ) MOLECULE TYPE: other nucleic acid ( x i ) SEQUENCE DESCRIPTION: SEQ ID NO:11:

```
ACTCTCTGTG TCTGACTCAT GCTCTCTCAG CATGAGTCAG ACAC        44
```

( 2 ) INFORMATION FOR SEQ ID NO:12:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:12:

```
CCTCTCGCTC GCCCCGCCCC GATCCTCTCG ATCGGGGCGG GGCGAG        46
```

( 2 ) INFORMATION FOR SEQ ID NO:13:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: circular ( i i ) MOLECULE TYPE: other nucleic acid ( x i ) SEQUENCE DESCRIPTION: SEQ ID NO:13:

```
CCTCTCGCTC GCCCCGCCCC GATCCTCTCG ATCGGGGCGG GGCGAG        46
```

( 2 ) INFORMATION FOR SEQ ID NO:14:

( i ) SEQUENCE CHARACTERISTICS:
        ( A ) LENGTH: 10 base pairs (B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:14:

KRGGCGKRRY 10

(2) INFORMATION FOR SEQ ID NO:15:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:15:

TTGGCNNNNN GCCAA 15

(2) INFORMATION FOR SEQ ID NO:16:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:16:

TTGGCNNNNN NGCCA 15

(2) INFORMATION FOR SEQ ID NO:17:

(i) SEQUENCE CHARACTERISTICS:
(A) LENGTH: 13 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:17:

GGTCACAGTG ACC 13

(2) INFORMATION FOR SEQ ID NO:18:

(i) SEQUENCE CHARACTERISTICS:
(A) LENGTH: 16 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:18:

YGGTWCAMWN TGTYCT 16

(2) INFORMATION FOR SEQ ID NO:19:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: other nucleic acid ( x i ) SEQUENCE DESCRIPTION: SEQ ID NO:19:

AGGTAAGATC AGGGACGT 18

( 2 ) INFORMATION FOR SEQ ID NO:20:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:20:

AGGGTATAAA AAGGGC 16

( 2 ) INFORMATION FOR SEQ ID NO:21:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:21:

ACCNNNNNNG GT 12

( 2 ) INFORMATION FOR SEQ ID NO:22:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:22:

TTTTTGGCT TTCGTTTCTG GGC 23

( 2 ) INFORMATION FOR SEQ ID NO:23:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:23:

ATCGGTGCAC CGAT 14

( 2 ) INFORMATION FOR SEQ ID NO:24:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:24:

GGGTATAAAT TCCGG 15

( 2 ) INFORMATION FOR SEQ ID NO:25:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:25:

AGGAAGTGAA A                                                                                       11

( 2 ) INFORMATION FOR SEQ ID NO:26:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:26:

GGCCACGTGA CC                                                                                  12

( 2 ) INFORMATION FOR SEQ ID NO:27:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:27:

CTTTGAGCAA                                                                                      10

( 2 ) INFORMATION FOR SEQ ID NO:28:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:28:

ARYCTTTGAC CTC                                                                             13

( 2 ) INFORMATION FOR SEQ ID NO:29:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:29:

TCTTTGACCT TGAGCCCAGC T                                                         21

( 2 ) INFORMATION FOR SEQ ID NO:30:

( i ) SEQUENCE CHARACTERISTICS:
        ( A ) LENGTH: 16 base pairs ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:30:

TGGTTAATNW TCNNCA                                                                                              16

( 2 ) INFORMATION FOR SEQ ID NO:31:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:31:

CTGTGGAATG                                                                                                     10

( 2 ) INFORMATION FOR SEQ ID NO:32:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:32:

GCTTTTCACA GCCCTTGTGG ATGC                                                                                     24

( 2 ) INFORMATION FOR SEQ ID NO:33:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:33:

AAGCCTGGGG CGTA                                                                                                14

( 2 ) INFORMATION FOR SEQ ID NO:34:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:34:

CCWWWWWWGG                                                                                                     10

( 2 ) INFORMATION FOR SEQ ID NO:35:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:35:

GTTCCCGTCA ATC  13

( 2 ) INFORMATION FOR SEQ ID NO:36:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:36:

GAAANNGAAA SK  12

( 2 ) INFORMATION FOR SEQ ID NO:37:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:37:

ANTCTCCTCC  10

( 2 ) INFORMATION FOR SEQ ID NO:38:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:38:

AACAATGGCT ATGCAGTAAA A  21

( 2 ) INFORMATION FOR SEQ ID NO:39:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:39:

AGAAAATGGT  10

( 2 ) INFORMATION FOR SEQ ID NO:40:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:40:

GNNTTGGTGA  10

( 2 ) INFORMATION FOR SEQ ID NO:41:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:41:

GWCACCTGTS CTTTTCCCTG                                            20

( 2 ) INFORMATION FOR SEQ ID NO:42:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:42:

AGTCAAGATG GC                                                         12

( 2 ) INFORMATION FOR SEQ ID NO:43:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:43:

CAGGCAGGTG GCCCA                                                    15

( 2 ) INFORMATION FOR SEQ ID NO:44:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:44:

AGGTCATGTG GCAAC                                                    15

( 2 ) INFORMATION FOR SEQ ID NO:45:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:45:

TAACCCAGGT GGTGTT                                              16

( 2 ) INFORMATION FOR SEQ ID NO:46:

( i ) SEQUENCE CHARACTERISTICS:
        ( A ) LENGTH: 14 base pairs

```
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:46:

AATTTCTCTC AAAT                                                          1 4

( 2 ) INFORMATION FOR SEQ ID NO:47:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( i i ) MOLECULE TYPE: other nucleic acid ( x i ) SEQUENCE DESCRIPTION: SEQ ID NO:47:

GTAACTCTCT TACCA                                                         1 5
```

OLIGONUCLEOTIDE DECOYS AND METHODS RELATING THERETO

This application is a 371 filing of PCT/US92/03205, filed Apr. 17, 1992 which is a continuation-in-part application of U.S. Ser. No. 07/687,337, filed Apr. 18, 1991, now abandoned, the entire contents of which are hereby incorporated by reference herein.

FIELD OF THE INVENTION

The present invention relates to novel oligodeoxynucleotides and novel oligonucleotides, and the use thereof to modulate the production of selected messenger or other cellular RNAs.

BACKGROUND OF THE INVENTION

The rate of transcription of many genes depends on the interaction of control proteins (e.g., transcription factors, repressors, and the like) with specific short DNA sequences, generally located close to the promoter. The CREB protein (also referred to as CRE-BP), for example, binds tightly to double-stranded DNA containing the sequence 5'-TGACGTCA-3'.

Double stranded DNA containing such a target sequence can be introduced into the system as a decoy, diverting control proteins from their endogenous DNA target. By diverting the control proteins from their endogenous target, the regulatory effects of such proteins can be altered.

Double stranded DNAs containing such a target sequence are typically prepared by first synthesizing the two complementary oligonucleotide strands, and then hybridizing them together. Introduction of such double stranded DNAs into whole cells, as will be required for many therapeutic applications, will be useful only if the construct is reasonably stable under physiological conditions under which cells remain viable. For example, if the sequence length of the double stranded DNA is insufficient, the two strands will tend to dissociate. In addition, relatively short DNA sequences will be particularly prone to nuclease digestion by enzymes in the growth medium.

Therefore, it would be desirable to develop DNA double-helixes which contain target sequences which bind to control proteins, and which are stable to physiological conditions which would otherwise degrade (and inactivate) such DNA.

BRIEF DESCRIPTION OF THE INVENTION

In accordance with the present invention, we have developed improved DNA structures which contain target sequences which bind to control proteins. The structures of the present invention are stable with respect to strand separation and to enzyme-mediated degradation, and are effective as decoys for control proteins, thereby enabling one to modulate the transcriptional control normally exerted by such control proteins.

DETAILED DESCRIPTION OF THE INVENTION

Figure 1:
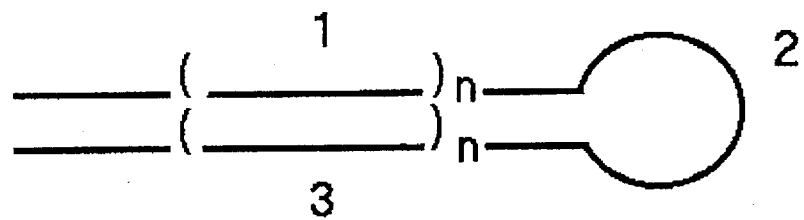
FIG. 1 is a schematic diagram of a hairpin DNA of the present invention.

In accordance with the present invention, there is provided a composition comprising an oligonucleotide comprising, reading from the 5'-end of said oligonucleotide:

(i) a first segment comprising a sequence of deoxynucleotide or nucleotide residues, or analogs thereof; wherein said first segment, when hybridized with its complement, forms at least one transcription control recognition sequence of at least 6 nucleotides, (ii) a second segment comprising a sequence of deoxynucleotide or nucleotide residues, or analogs thereof, sufficient to allow the formation of a first loop structure between said first segment and the third segment, and (iii) a third segment comprising a sequence of deoxynucleotide or nucleotide residues, or analogs thereof, wherein said third segment is substantially the complement to said first segment.

In accordance with another embodiment of the present invention, there is provided a composition comprising a double-stranded DNA fragment, wherein said DNA fragment contains at least one transcription control recognition sequence of at least 6 nucleotide base pairs, and wherein one strand of said DNA fragment is attached to the other strand by means of at least one linker that is covalently bound to each of the strands of said DNA.

In accordance with yet another embodiment of the present invention, there is provided a method to modulate the transcription of products which are subject to regulation by transcription control recognition sequences, said method comprising administering a therapeutically effective amount of at least one of the above-described compositions to a subject. In accordance with still another embodiment of the present invention, there is provided a method to improve the stability of a double-stranded DNA fragment, wherein said DNA fragment contains at least one transcription control recognition sequence of at least 6 nucleotide base pairs, said method comprising introducing at least one linker between the first strand and the strand complementary thereto, wherein said linker is covalently bound to each strand of said double-stranded DNA fragment.

In accordance with still another embodiment of the present invention, there is provided a method to reversibly crosslink oligonucleotides to polypeptides which recognize the oligonucleotide sequence. This method involves synthesizing oligonucleotides as described above, wherein one or more phosphorothioate diester linkages are incorporated into said oligonucleotide, allowing the phosphorothioate diester-containing oligonucleotide to bind to polypeptides which recognize the sequence of said oligonucleotide, then contacting the polypeptide-bound oligonucleotide with a transition metal reagent such as $K_2PtCl_4$. The effects of crosslinking can readily be reversed by treating the crosslinked material with an effective ligand for the transition metal, such as an alkali metal cyanide, and the like.

Transcription control recognition sequences contemplated by the present invention are sequences which are recognized by control proteins, and which are involved in either enhancing or repressing transcription of associated sequences. Transcription control recognition sequences contemplated by the present invention include sequences set forth in the article by Locker and Buzard in J. DNA Sequencing and Mapping 1: 3–11 (1990), and include promoter elements, hormone response elements, viral and cellular elements, liver associated elements, tissue associated elements, and the like.

Exemplary promoter elements include the CACCC-Box (having the sequence 5'-GCCACACCC-3'), the GC-Box (having the sequence 5'-KRGGCGKRRY-3', SEQ ID NO: 14, wherein each K is independently G or T; each R is independently G or A; and Y is C or T), the CAT-Box of NF-1 cells (having the sequence 5'-TTGGCNNNNNGCCAA-3' or 5'-TTGGCNNNNNNGCCA-3', SEQ ID NO: 15 and 16, respectively, wherein each N is independently selected from A, G, C or T), and the like.

Exemplary hormone response elements include the estrogen response element (having the sequence 5'-GGTCACAGTGACC-3'; SEQ ID NO: 17), the glucocorticoid response element (having the sequence 5'-YGGTWCAMWNTGTYCT-3', SEQ ID NO: 18, wherein each Y is independently C or T; each W is independently A or T; M is A or C; and N is any one of A, C, G, or T), the thyroid hormone response element (having the sequence 5'-AGGTAAGATCAGGGACGT-3'; SEQ ID NO: 19), the thyroid hormone inhibitory element (having the sequence 5'-AGGGTATAAAAAGGGC-3'; SEQ ID NO: 20), the sterol-dependent repressor (having the sequence 5'-GTGSGGTG-3', wherein S is G or C), and the like.

Exemplary viral elements include the papillomavirus E2 enhancer (having the sequence 5'-ACCNNNNNNGGT-3', SEQ ID NO: 21, wherein each N is independently selected from A, C, G or T), the adenovirus enhancer-3 (having the sequence 5'-TTTTTTGGCTTTCGTTTCTGGGC-3'; SEQ ID NO: 22), the EII-ORFP (Adeno) element (having the sequence 5'-ATCGGTGCACCGAT-3'; SEQ ID NO: 23), the ESV IE promoter (having the sequence 5'-TAATGARAT-3', wherein R is A or G), the ESV late promoter (having the sequence 5'-GGGTATAAATTCCGG-3'; SEQ ID NO: 24), and the like.

Exemplary viral and cellular elements include the E2F (Adeno) element (having the sequence 5'-TTTCGCGC-3'), the EIIaE-Cβ (Adeno) element (having the sequence 5'-TGGGAATT-3'), the E4IF1 (Adeno, CMV) element (having the sequence 5'-AGGAAGTGAAA-3'; SEQ ID NO: 25), the Adenovirus major late transcription factor, UEF, USF (having the sequence 5'-GGCCACGTGACC-3'; SEQ ID NO: 26), and the like.

Exemplary liver associated elements include the AFP Box I (having the sequence 5'-CTTTGAGCAA-3'; SEQ ID NO: 27), the Liver factor-A1, ENF-2 element (having the sequence 5'-TGRMCC-3', wherein R is A or G; and M is A or C), the tf-LF1 (FRI) element (having the sequence 5'-ARYCTTTGACCTC-3'; SEQ ID NO: 28, wherein R is A or G; and Y is C or T), the tf-LF2 (DRI) element (having the sequence 5'-TCTTTGACCTTGAGCCCAGCT-3'; SEQ ID NO: 29), LF-B1 (EKF-1, B-Protein, Liver element, PE, EP-1, AFP1), having the sequence 5'-TGGTTAATNWTCNNCA-3', SEQ ID NO: 30, wherein W is A or T; and each N is independently selected from A, C, G, or T; the C/EBP (EBP-20) element (having the sequence 5'-TCNTACTC-3'), and the like.

Additional exemplary elements include general elements [e.g., the AP-1 element (having the sequence 5'-TGAGTCAG-3'), the AP-2 element (having the sequence 5'-GSSWGSCC-3', wherein each S is independently C or G; and W is A or T), the AP-3 element (having the sequence 5'-GGAAAGTCC-3'), the AP-4 element (having the sequence 5'-CAGCTGTGG-3'), the AP-5 element (having the sequence 5'-CTGTGGAATG-3'; SEQ ID NO: 31), the CRE-BP element (having the sequence 5'-TGACGTCA-3'), the 3'-enhancer of sequence 5'-GCTTTTCACAGCCCTTGTGGATGC-3'; SEQ ID NO: 32), the fos basal level inhibitor (having the sequence 5'-GCGCCACC-3'), the fos BLE-2 element (having the sequence 5'-AAGCCTGGGGCGTA-3'; SEQ ID NO: 33), serum response element (having the sequence 5'-CCWWWWWWGG-3', SEQ ID NO: 34, wherein each W is independently selected from A or T), the SIS-conditioned medium response element (having the sequence 5'-GTTCCCGTCAATC-3'; SEQ ID NO: 35), the α-interferon viral response element (having the sequence 5'-GAAANNGAAASK-3', SEQ ID NO: 36, wherein each N is independently A, C, G or T; S is C or G; and K is C or T), the α-Interferon Silencer A (having the sequence 5'-GAAAGY-3', wherein Y is T or C), the β-Interferon Silencer B (having the sequence 5'-TCMYTT-3', wherein M is A or C; and Y is C or T), the Lysozyme Silencer 1 (having the sequence 5'-ANCCTCTCY-3'), the Lysozyme Silencer 2 (having the sequence 5'-ANTCTCCTCC-3'; SEQ ID NO: 37), the Lysozyme Silencer 3 (having the sequence 5'-AACAATGGCTATGCAGTAAAA-3'; SEQ ID NO: 38), the Myc-CF1 element (having the sequence 5'-AGAAAATGGT-3'; SEQ ID NO: 39), the TGF-β inhibitory element (having the sequence 5'-GNNTTGGTGA-3'; SEQ ID NO: 40), and the like], tissue associated elements [e.g., pancreatic enhancer (having the sequence 5'-GWCACCTGTSCTTTTCCCTG-3'; SEQ ID NO: 41), keratinocyte enhancer (having the sequence 5'-AANCCAAA-3'), immunoglobulin gene enhancers, such as the µE1 enhancer (having the sequence 5'-AGTCAAGATGGC-3'; SEQ ID NO: 42), the µE2 enhancer (having the sequence 5'-CAGGCAGGTGGCCCA-3'; SEQ ID NO: 43), the µE3 enhancer (having the sequence 5'-AGGTCATGTGGCAAC-3'; SEQ ID NO: 44), the µE4 enhancer (having the sequence 5'-TAACCCAGGTGGTGTT-3'; SEQ ID NO: 45), and the like], as well as other such elements.

In accordance with the present invention, the effect of control proteins on the above-described transcription control recognition sequences can be modulated by administration to a subject of compositions of the invention containing the appropriate recognition sequences. Thus, for example, the induction of hormone response can be modulated by the administration of a decoy having one of the hormone recognition sequences set forth above. Similarly, the expression of oncogenes (e.g., genes related to myc, jun, fos, etc), viral enhancers, and the like, can be modulated by the administration of a decoy containing an appropriate recognition sequence. By turning off the expression of oncogenes in this way, it becomes possible for the cell population being treated to return to its normal state. By turning off the expression of viral enhancers, the proliferation of viral species can be prevented, thereby enabling the host organism to resist viral infection.

The compositions of the present invention can be provided to a subject by any suitable means of administration, as are well known to those of skill in the art, such as for example, by injection (when formulated in a suitable carrier), by topical application (when formulated in a suitable carrier), by incorporation into liposomes, which are then administered in conventional manner, or targeted to recipient cells by specific antibodies, and the like.

Figure 2:
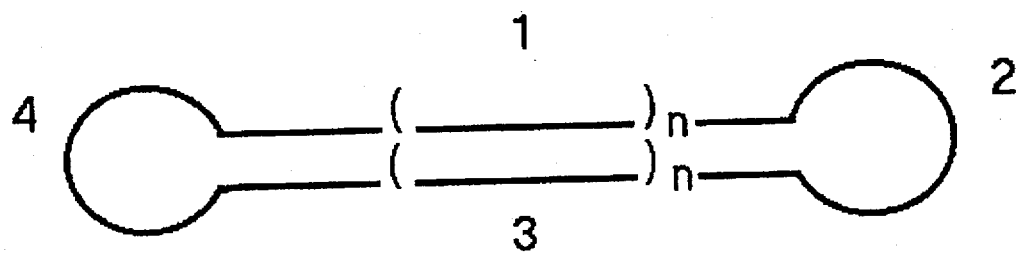
FIG. 2 is a schematic diagram of a dumbbell DNA of the present invention.
Figure 4:
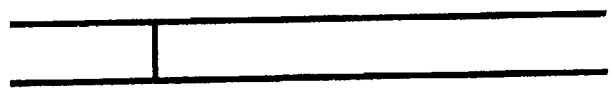
FIG. 4 is a schematic diagram of covalently bound DNA of the present invention.
Figure 3A:
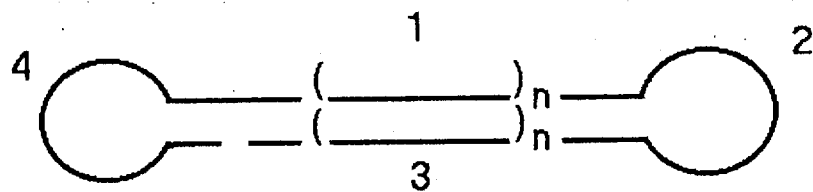
FIGS. 3A–3F are schematic diagrams of several modified forms of the dumbbell DNA of the present invention.
Figure 3B:
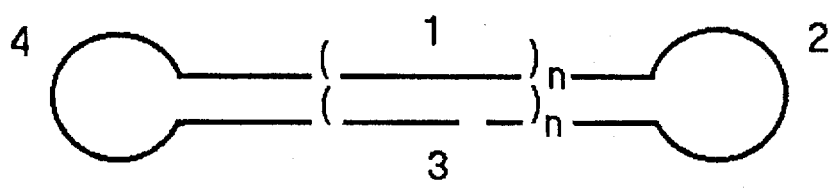
Figure 3C:
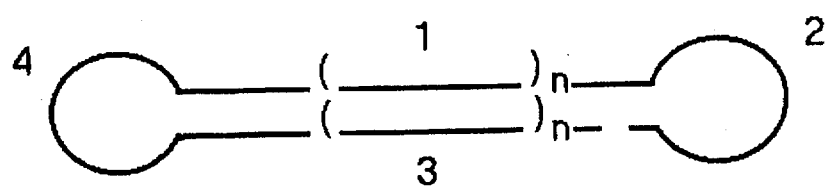
Figure 3D:
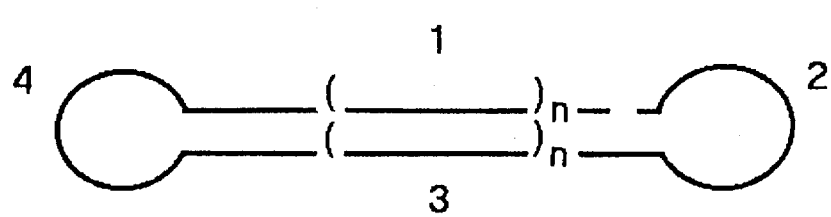
Figure 3E:
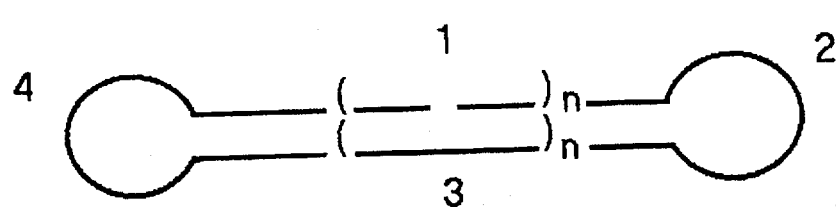
Figure 3F:
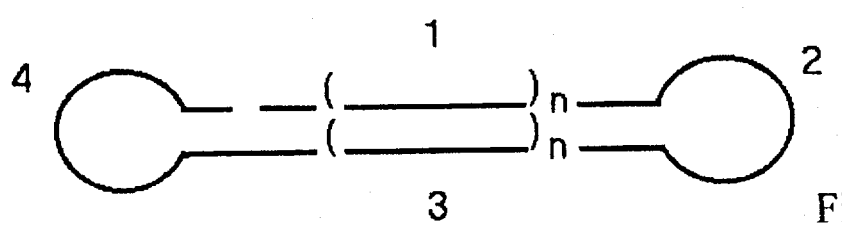

Structures contemplated by the present invention include "hairpin" structures (see FIG. 1); "dumbbell" structures (see FIG. 2); modified dumbbell structures (see FIGS. 3A–3F); "cross-linked" decoy structures, i.e., double stranded structures which are covalently attached to one another by at least one linker that is covalently linked to each of the strands of the decoy (see FIG. 4); and the like.

Loop structures contemplated for use in the practice of the present invention comprise at least three nucleotides linking one strand of the decoy to the other. Typically, loop structures will comprise in the range of about 3 up to 10 nucleotides, with loop structures of 5 nucleotides being presently preferred.

Dumbbell structures contemplated for use in the practice of the present invention comprise a loop structure as described above at each end of the decoy, thereby forming a closed circular DNA. Those of skill in the art recognize that one or more of the nucleotide bonds of either of the hybridized chains of the dumbbell can be broken, without disrupting the basic double helix structure of the dumbbell. Thus, modified dumbbell structures are also contemplated by the present invention (see FIGS. 3A–3F). Such modified structures include those containing one or more breaks in the nucleotide bonds of the oligonucleotide chain. Optionally, the oligonucleotide can be dephosphorylated at the site of the break, and/or can actually be missing one or more of the bases normally present at the site of the break, so long as the geometry required to present the transcription control recognition sequence to the target control protein is not substantially altered.

In designing the oligonucleotides of the invention, in addition to incorporating the deoxynucleotides, nucleotides, or analogs thereof required to make up the transcription control recognition sequence(s), and the loop structure(s), "spacer" nucleotides can also be incorporated into the oligonucleotide. Thus, the invention oligonucleotide can include additional nucleotide sequences which are not part of the transcription control recognition sequence(s), or the loop structure(s). While there is no requirement that spacer nucleotides be incorporated into the oligonucleotide of the present invention, up to 30 nucleotides or more can be present, in addition to the transcription control recognition sequence(s) and the loop structure(s).

While the oligonucleotides of the invention contain at least one transcription control recognition sequence, those of skill in the art recognize that the invention compositions can contain multiple transcription control recognition sequences. Such oligonucleotides can contain multiple repeats of the same transcription control recognition sequence, or one or more copies of more than one transcription control recognition sequence. While, in theory, there is no limit as to the number of transcription control recognition sequences which can be included in a single oligonucleotide of the invention, generally, ten or fewer transcription control recognition sequences will be included in a single oligonucleotide.

Alternative means to link the complementary strands of the transcription control recognition sequence include covalently linking one strand to the other by means of a linker such as a (poly)alkylene (e.g., a (poly)methylene) bridge, an α,ω-poly(alkylene)dicarboxylic acid, a binuclear $Pt^{II}$ complex, such as for example:

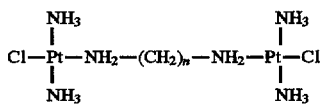

wherein n is 4, 5, or 6. Another alternative means to link the complementary strands of the transcription control recognition sequence is to contact the complementary strands of the transcription control recognition sequence with the natural product, psoralen, then photo-crosslinking by exposure to ultraviolet light, and the like.

Preparation of the invention structures can be carried out employing standard synthetic techniques. For example, to prepare a hairpin DNA of the invention, a single strand of DNA having the desired sequence of nucleotides and/or nucleotide analogs can be prepared on a DNA synthesizer, then allowed to self-associate.

To prepare a dumbbell DNA of the invention, a single strand of DNA having the desired sequence of nucleotides and/or nucleotide analogs can be prepared on a DNA synthesizer, phosphorylated with an appropriate oligonucleotide kinase, then allowed to self-associate, to form a dumbbell structure having a break where the two ends of the synthetic oligonucleotide meet. Thereafter, the break in the dumbbell structure can be annealed (employing, for example, DNA ligase) to produce a closed, circular DNA.

Oligonucleotides contemplated for use in the practice of the present invention can be prepared from naturally occurring nucleotides or deoxynucleotides (A, C, G, T, or U), as well as nuclease resistant analogs thereof (e.g., phosphorothioates, methylphosphonates, phosphoramidates, and the like).

Optionally, oligonucleotides employed in the practice of the present invention can be modified by incorporating one or more phosphorothioate diester linkages therein. The resulting modified oligonucleotides are useful, for example, for the transition metal catalyzed crosslinking of oligonucleotide to polypeptide bound thereto.

The phosphorothioate diester linkages are readily incorporated into the oligonucleotide during synthesis by replacing the reagent used for oxidation of the phosphite intermediate (typically iodine is used for this purpose) with a sulfurizing agent such as tetraethylthiouram disulfide.

At least one phosphorothioate diester linkage will be incorporated into the synthesized oligonucleotide to facilitate crosslinking thereof with polypeptide. Preferably, several phosphorothioate diester linkages will be incorporated into the oligonucleotide. In a presently preferred embodiment, at least four or more phosphorothioate diester linkages are incorporated into the recognition sequence of the oligonucleotide (i.e., the portion of the oligonucleotide which is recognized by the target polypeptide).

Suitable crosslinking catalysts for use in the practice of the present invention include transition metal catalysts such as Pt(II) compounds, including Pt(II) complexes. Examples of such compounds include $K_2PtCl_4$, trans platinum diammine dichloride, and the like.

The invention will now be described in greater by reference to the following non-limiting examples.

EXAMPLE I

The following oligomers, containing the core 8-mer recognition sequence for the CRE-BP (5'-TGACGTCA-3'), were synthesized using standard oligonucleotide synthesis techniques.

1. Two complementary 18-mer sequences containing the core CRE-BP 8-mer recognition sequence with 5 flanking bases on either side:

5'-AAA TTG ACG TCA TGG TAA-3' (SEQ ID No. 1)
3'-TTT AAC TGC AGT ACC ATT-5' (SEQ ID No. 2)

2. A 41-mer containing the above complementary 18-mer sequences, with the 3' end of Sequence ID No. 1 joined to the 5' end of Sequence ID No. 2 by a 5-base CTCTC loop, as follows (SEQ ID NO: 3):

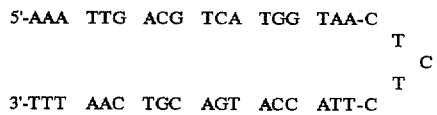

3. A 46-mer containing the above complementary 18-mer sequences, designed such that it forms a looped self structure with a nicked gap between the 3'-OH and 5'-OH tail ends (SEQ ID NO: 4):

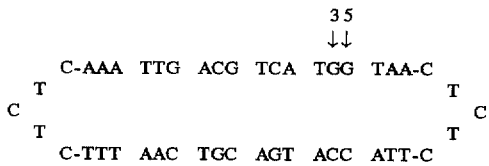

The nicked oligomer can then be phosphorylated with T4 polynucleotide kinase and ligated with DNA ligase to give a closed, circular, self-complementary structure (SEQ ID NO: 5):

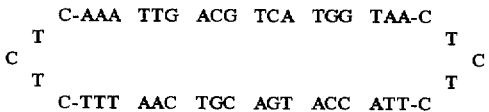

Each of the above oligomers was labeled with [$^{32}$P] at their 5' ends. 0.01–0.02 optical density units (ODUs) were incubated with 2 µM of gamma-[$^{32}$P]-ATP (specific activity of 3 µCi/pmole) and 20 units of polynucleotide kinase in 50 ml of buffer containing 50 mM Tris, pH 7.6, 10 mM MgCl$_2$, 5 mM DTT and 0.1 mM EDTA for 45 minutes at 37° C. The reaction was stopped with 2 µl of 0.5M EDTA and the enzyme removed by extraction with phenol/chloroform.

The 5'-[$^{32}$P]-labeled oligomers were separated from any unkinased starting material by HPLC on RPC-5 at pH 12, using a 0.03M–0.13M Tris-perchlorate elution gradient.

The 5'-[$^{32}$P]-labeled oligomers were then purified on a Nensorb purification cartridge.

1–5 pmoles of the 5'-[$^{32}$P]-labeled 46-mer was reacted with 4 units of DNA ligase overnight at room temperature in 50 µl of buffer containing 50 mM Tris pH 7.5, 5 mM MgCl$_2$, 0.5 mM ATP, and 0.5 mM DTT.

The ligated product was separated from unligated starting material by denaturing gel electrophoresis on 12% acrylamide. The ligated product had a higher mobility than the unligated product and was resistant to alkaline phosphatase treatment, whereas the 5'-[$^{32}$P]-label was removed from the unligated material by this enzyme.

To study the ability of the oligonucleotides of the invention (Sequence ID Nos. 3, 4 and 5) to bind to CRE-BP, 0.015 pmole of the [$^{32}$P]-labeled 41-mer, 46-mer, or the ligated 46-mer was incubated with either 200 ng of pure CRE-BP or a nuclear cell extract (obtained from PC12 cells) containing 4 ng of protein. Incubation was carried out for 20 minutes at room temperature in 5 µl of buffer containing 15 mM Tris pH 7.5, 50 mM KCl, 0.1 mM EDTA, 0.5 mM DTT and 9 µg/ml of acetylated bovine serum albumin. As a comparison, the [$^{32}$P]-labeled double-stranded 18-mer (i.e., the result of hybridizing Sequence ID Nos. 1 and 2) was incubated in the presence of the same reagents and under the same conditions.

Binding of the [$^{32}$P]-labeled oligomers to CRE-BP was determined by a gel shift assay on a 6% polyacrylamide non-denaturing gel. Electrophoresis was carried out at 7 ma for approximately 2.5 hours. The gels were then autoradiographed.

Binding of the [$^{32}$P]-labeled oligomers to CRE-BP could be seen as a much slower-moving band near the origin of the gel, whereas the unbound oligomer had a considerably higher mobility.

The double-stranded 18-mer, 41-mer and both the unligated and ligated forms of the 46-mer were bound to both pure CRE-BP and CRE-BP in the crude nuclear extract. The ligated 46-mer bound more efficiently to CRE-BP than did any of the other oligomers.

Cross-linking of the ligated CRE-BP oligomer to CRE-BP was carried out after the above-described binding assay had been performed. Cross-linking was carried out by adding 1 µl of a 0.5 mM transplatinum diammine dichloride solution to 5 µl of the binding reaction mixture, and left at room temperature for 1 hour.

Protein bound (but not cross-linked) to the oligomer, was dissociated from the oligomer by adding SDS to a final concentration of 0.1%. Oligomers that are cross-linked to the protein are not dissociated by SDS, and can be visualized on an 8% SDS gel.

Approximately 20% of the oligomer originally bound to CRE-BP was cross-linked to the protein by treatment with the transplatinum diammine dichloride solution.

The stability of the CRE-BP/oligomer complexes to degradation upon exposure to enzymes in both human and fetal calf serum was measured as follows:

Each [$^{32}$P]-labeled oligomer (~1 pmole/ml) was incubated in 100% human serum or 10% fetal calf serum in RPM1 1640 media (Hazelton Labs) at 37° C. for times ranging from 10 minutes to 24 hours. Aliquots of serum were diluted with buffer and analyzed on a 20% denaturing gel (20% polyacrylamide gel containing 7M urea at pH 8.2).

Results indicated that after 30 minutes, 50–75% of the single stranded oligomer had been degraded in both human and calf serum. The double-stranded 18-mer was 50–60% degraded in both sera after 24 hours. The 41-mer was still stable after 24 hours at 37° C. in 10% fetal calf serum, but was ~20% degraded after 24 hours at 37° C. in 100% human serum. Dramatically, there was no discernible degradation of the ligated oligomer in either calf or human serum, even after treatment for 24 hours at 37° C.

EXAMPLE II

As another application of the invention oligonucleotides, the double-stranded phosphorothioate oligonucleotides described by Bielinska et al. [Science 250: 997–1000 (1990)] could be improved in stability by introducing at least one loop structure therein. Thus, the Bielinska double-stranded phosphorothioate probe (SEQ ID NO: 6):

5'-AAA TTT ACA TAT TAC ACA TAT-3'

3'-TTT AAA TGT ATA ATG TGT ATA-5' which the authors show to be capable of combining with the IL-2 octamer transcription factor (thereby inhibiting the expression of proteins under the control of the octamer sequence enhancer in Jurket cells), could be replaced with a phosphorothioate hairpin of the structure (SEQ ID NO: 7):

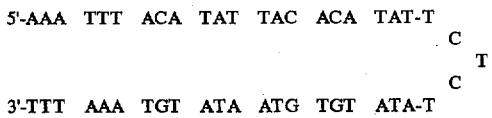

The hairpin structure should be much more resistant to the effects of enzyme-mediated degradation, denaturation, and the like.

In a similar experiment, the Bielinska double-stranded phosphorothioate probe (SEQ ID NO: 8):

5'-AGG GAC TTT CCG CTG GGG ACT TTT C-3'
3'-TCC CTG AAA GGC GAC CCC TGA AAA G-5' is shown to be capable of depressing transcription from the HIV enhancer in clone 13 cells. This sequence could be replaced with a phosphorothioate hairpin of the structure (SEQ ID NO: 9):

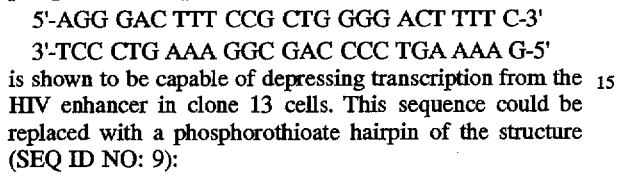

The hairpin structure should be much more resistant to the effects of enzyme-mediated degradation, denaturation, and the like.

EXAMPLE III

The following were obtained from commercial sources: $K_2PtCl_4$ (Pfaltz and Bauer); trans platinum diammine dichloride (transPt$^{II}$), cis platinum diammine dichloride (cisPt$^{II}$) and (poly[dI-dC].poly[dI-dC]) (from Sigma); T4 DNA ligase (Gibco-BRL); and tetraethylthiouram disulfide (TETD)/acetonitrile (Applied Biosystems). The purified CREB protein and a CREB-containing nuclear extract from PC12 cells were gifts for Dr. Marc Montminy [see Montminy and Bilezikjian in Nature 328:175–178 (1987); and Yamamoto et al., in Nature 334:494–498 (1988)]; the purified JUN protein was a gift from Dr. Inder Verma [see Bohmann et al., in Science 238:1386–1392 (1987); and Angel et al., in Nature 332:166–171 (1988)].

Dumbbell oligonucleotides containing the double-stranded CRE, TRE and Sp1 recognition sequences (SEQ ID NOs: 5, 11, and 13, respectively) were obtained by synthesizing linear oligonucleotides (SEQ ID NOs: 4, 10, and 12, respectively) on an Applied Biosystems model 391 PCR MATE automated DNA synthesizer using phosphoramidite chemistry, and then ligating with T4 DNA ligase. Phosphorothioate linkages were introduced using the sulfurizing reagent TETD/acetonitrile in place of $I_2$ during the oxidation step in the synthesis cycle. This necessitated synthesizing the oligomer in sequential steps with a break in synthesis when the $I_2$ reagent was replaced by TETD/acetonitrile and vice versa. The synthesizer is reprogrammed before and after each introduction of a phosphorothioate residue, the already synthesized sequence fulfilling the role usually played by the resin-attached initiating monomer.

Thus a sequence 5'-$N_1N_2N_3N_4$(s)$N_5N_6N_7$-3' would be made by first synthesizing the sequence 5'-$N_5N_6N_7$-3' in the usual way. The iodine reagent is then replaced by TETD/acetonitrile, and the sequence $N_4X$ is programmed, where X stands for the 5'-$N_5N_6N_7$-3' sequence that is already attached to the resin and is treated as if it were the resin attached 3'-nucleoside in a standard synthesis. The synthetic program is modified as indicated in the instructions provided with the sulfurizing reagent and $N_4$ is incorporated into the sequence via a phosphorothioate linkage. The sulfurizing reagent is then replaced by the iodine reagent and the sequence 5'-$N_1N_2N_3X$-3' is programmed, using the normal synthetic cycle program.

The synthesis of 5'-tritylated CRE(s)$_6$-46mer (SEQ ID NO: 4), for example, was carried out by synthesizing the following sequence in turn, with the sulfurizing reagent replacing the iodine reagent at the residues indicated by an (s):

1) 5'-ATG-3'; 2)5'-C(s)X-3';
3) 5'-GTX-3'; 4)5'-C(S)X-3';
5) 5'-GAX-3'; 6)5'-T(s)X-3';
7) 5'-AAT TTC TCT CAA ATX-3' (SEQ ID NO: 46);
8) 5'-C(s)X-3'; 9)5'-GTX-3';
10) 5'-C(s)X-3'; 11)5'-GAX-3';
12) 5'-T(s)X-3';
13) 5'-GTA ACT CTC TTA CCA X-3' (SEQ ID NO: 47);

where "X" stands for the resin-attached oligomer.

After deprotection with ammonia, the 5'-tritylated phosphorothioate oligonucleotides were detritylated on an OPC oligonucleotide purification column (Applied Biosystems) and further purified by denaturing gel electrophoresis on 12% acrylamide. (The oligonucleotides were heated at 70° C. for 3 minutes prior to loading on the gel). The phosphorothioate-containing oligonucleotides had longer retention times than the standard oligomers when analyzed by HPLC on an RPC-5 column. They gave multiple peaks due to the presence of R- and S- isomers at each phosphorothioate group. After oxidation with $I_2$ [Connolly et al., Biochemistry Vol. 23:3443–4453 (1984)], they were converted to oligonucleotides containing normal phosphodiester bonds that gave a sharp, single peak on RPC-5. Oligonucleotides were phosphorylated at their 5'-termini using $\gamma$-[$^{32}$P]-ATP and polynucleotide kinase. The kinased products were purified on a Nensorb DNA purification column (Du Pont), but were not separated from the starting oligomer at this stage.

To ligate the nicked dumbbell forms of 5'-[$^{32}$P]-oligonucleotides or their phosphorothioate-containing analogues (SEQ ID NOs: 4, 10, and 12, respectively), ~1–20 pmoles of the linear oligonucleotide was heated at 65° C. for 3 minutes in 36 µl of water. Then 10 µl of a 5×ligase buffer were added so that the final reaction mixture contained 50 mM Tris (pH 7.8), 10 mM $MgCl_2$, 1 mM ATP, 1 mM DTT and 5% polyethylene glycol. After 10 minutes at room temperature, 4 units (4 µl) of DNA ligase was added. After overnight incubation at room temperature, the reaction mixture was heated at 75° C. for 3 minutes. The ligated product was then separated from non-ligated starting material by denaturing gel electrophoresis on 12% polyacrylamide. The ligated form, which is resistant to the action of alkaline phosphatase, migrates faster than the unligated form. Yields of ligated product ranged from 50–95% for standard oligodeoxynucleotides and from 40–70% for phosphorothioate-containing oligomers.

Binding of the ligated CRE and CRE(s)$_6$ sequences to the CREB protein was carried out as previously described [Dwarki et al., EMBO J. 9:225–232 (1990); chu and Orgel, Nucleic Acids Res. 19:6958 (1991)]. Approximately 0.015 pmole of the [$^{32}$P]-CRE sequences was added to ~200 ng of pure CREB protein in 10 µl of buffer containing 50 mM KCl, 15 mM Tris, (pH 7.5), 0.1 mM EDTA, 0.5 mM DTT, 180 ng acetylated BSA and 250 ng (poly[dI-dC].poly[dI-dC]) and then incubated at room temperature for 15–20 minutes. Binding was detected by gel shift assay on 6% non-denaturing gels using 40 mM Tris-borate at pH 8.2 as the electrophoresis buffer. Binding of the ligated CRE sequences to an aliquot of nuclear extract from PC12 cells (4 μg total protein) was carried out in the same way. Binding of TRE sequences to the JUN protein was carried out similarly in 10 μl of buffer containing 50 mM Tris (pH 7.9), 100 mM KCl, 1 mM EDTA, 1 mM DTT, 12.5 mM $MgCl_2$, 20% glycerol and 250 ng (poly[dI-dC]·poly[dI-dC]). Binding was detected by non-denaturing gel electrophoresis on 6% acrylamide, using 20 mM Tris-borate (pH 8.2) as electrophoresis buffer.

For crosslinking of oligonucleotide to protein, approximately 0.015 pmole of the appropriate [$^{32}$P]-labelled dumbbell oligonucleotide was first incubated with 200 ng CREB or JUN protein in 10 μl of buffer containing 50 mM KCl, 15 mM Tris (pH 7.5), 0.1 mM EDTA, 0.06 mM DTT, 180 ng acetylated BSA and 250 ng (poly[dI-dC]·poly[dI-dC]) as described above. After 15 minutes at room temperature, 1–3 μl of a freshly prepared solution containing the required amount of $K_2PtCl_4$ or transPt$^{II}$ in buffer containing 1 mM phosphate (pH 7) and 0.1 mM EDTA was added to the reaction mixture. Incubation was continued at room temperature in the dark for 1 hour. 0.5 μl of a 5% solution of SDS was then added and the crosslinked product separated from non-crosslinked oligonucleotide on an 8% polyacrylamide gel using buffer containing 90 mM Tris-borate (pH 8.2) and 0.1% SDS (SDS gels disrupt noncovalently associated DNA-protein complexes).

It is shown above that the double-stranded CRE recognition sequence contained in a ligated dumbbell oligonucleotide binds to the CREB protein just as efficiently as does normal hybridized double-stranded DNA sequence. Similar results have been obtained for the TRE dumbbell sequence and the JUN protein [Chu and Orgel (1991) supra]. In further studies, it has been found that the introduction of 6 phosphorothioate residues within the octamer recognition sequence of ligCRE(s)$_6$ (see SEQ ID NO: 5) or ligTRE(s)$_6$ (see SEQ ID NO: 11) does not diminish their binding efficiency to CREB or JUN, respectively. Similar results have been reported for the interaction of phosphorothioate-containing DNA with other proteins [Bielinska et al., Science Vol. 250:997–1000 (1990)].

Crosslinking of ligCRE(s)$_6$—CREB and ligTRE(s)$_6$—JUN with $K_2PtCl_4$

An autoradiogram of an 8% SDS gel, after [$^{32}$P]ligCRE(s)$_6$ has been crosslinked to CREB in the presence of 0.3 mM $K_2PtCl_4$ or 2 mM $K_2PtCl_4$ shows 2 bands which correspond to proteins of approximate molecular weights 100,000 and 52,000. It is believed that the 100,000 M.W. band corresponds to the dumbbell oligomer (M.W. 16,000) bound to dimeric CREB protein (86,000) [Montminy and Bilezikjian, Nature Vol. 328:175–178 (1987)], and the 52,000 band corresponds to the oligomer bound to monomeric CREB protein. The proportion of crosslinked product in the dimeric form increases as the platinum concentration is increased. In contrast, no bands are visible when the crosslinking procedure is carried out in the absence of CREB.

The crosslinking efficiency of [$^{32}$P]ligCRE(s)$_6$ was compared with that of [$^{32}$P]ligCRE (i.e., the same ligated dumbbell sequence, but containing normal phosphodiester linkages) and [$^{32}$P]ligSp1(s)$_6$ (see SEQ ID NO: 13) (an unrelated dumbbell oligomer containing 6 phosphorothioate residues within the octamer Sp1 recognition sequence). Also included for comparison was a crosslinking mixture that contained [$^{32}$P]ligCRE(s)$_6$ and an 80-fold excess of the unligated oligomer without a [$^{32}$P]-label; and a crosslinking reaction that contained a hundredfold excess of an unlabelled, unrelated sequence containing 6 phosphorothioate residues.

Comparison of [$^{32}$P]ligCRE(s)$_6$ with [$^{32}$P]ligCRE indicates that the presence of internal phosphorothioate residues within the DNA recognition binding region is responsible for the efficient crosslinking of ligCRE(s)$_6$ to CREB. When the same circular dumbbell CRE sequence contained only normal phosphodiester bonds, the crosslinking efficiency was reduced by 80%. At lower platinum concentrations (0.3 mM), crosslinking was not visible when the non-substituted oligonucleotide was used.

These results also indicate that the crosslinking of the ligCRE(s)$_6$ to CREB is sequence specific. Addition of an 80-fold excess of the same unlabelled (but unligated) phosphorothioate sequence to the crosslinking reaction decreased the yield of crosslinked product by 85–90%, but no decrease in crosslinked product was visible when an unrelated circular sequence containing 6 internal phosphorothioate residues was added to the crosslinking mixture. Furthermore, a dumbbell oligomer containing 6 phosphorothioate residues in the Sp1 recognition octamer sequence crosslinked to CREB with less than 10% of the efficiency of the CRE sequence at a high platinum concentration (2 mM). No crosslinking could be detected with an intermediate platinum concentration (0.3 mM).

When the number of pmoles of ligCRE(s)$_6$ crosslinked to CREB, as estimated by SDS gel electrophoresis, was compared to the number of pmoles that were bound to CREB as estimated in an independent experiment using non-denaturing gel electrophoresis, the crosslinking efficiency was found to be 40–50% of the binding efficiency when the concentration of $K_2PtCl_4$ was 2.3 mM. Lowering the $K_2PtCl_4$ concentration to 0.3 mM resulted in a 20–30% crosslinking efficiency, and raising the concentration to 4 mM resulted in a 60–70% crosslinking efficiency.

Very similar results are obtained when [$^{32}$P]ligTRE(s)$_6$ (see SEQ ID NO: 11) is crosslinked to JUN. [$^{32}$P]ligTRE, containing normal phosphodiester bonds, crosslinks with approximately 15% of the efficiency of the [$^{32}$P]ligTRE(s)$_6$ when the concentration of $K_2PtCl_4$ is 2 mM. No crosslinking of [$^{32}$P]ligTRE is visible when the concentration of $K_2PtCl_4$ is 0.3 mM. Crosslinking is inhibited by 85% when an 80-fold excess of unlabelled unligated TRE(s)$_6$ is added to the crosslinking reaction mixture, but a 100-fold excess of a random oligomer containing the same number of phosphorothioate residues does not inhibit crosslinking. A dumbbell [$^{32}$P]ligSp1(s)$_6$ sequence (see SEQ ID NO: 13) crosslinks to JUN with less than 10% of the efficiency of ligTRE(s)$_6$. The molecular weight of the crosslinked product indicates that crosslinking occurs between [$^{32}$P]ligTRE(s)$_6$ and monomeric JUN.

TransPt$^{II}$ forms crosslinks between CRE and CREB or TRE and JUN efficiently at concentrations considerably lower than those needed to crosslink with $K_2PtCl_4$. However, even at relatively low concentrations of transPt$^{II}$ (0.08 mM), aggregates form that stick to the origin of SDS gels. CisPt$^{II}$ was not an effective crosslinking agent.

By treating Pt-crosslinked products with 0.4M NaCN overnight at room temperature, the cyanide ion displaces the platinum complex from the phosphorothioate groups and releases the labelled oligonucleotides ligCREB(s)$_6$ or ligTRE(s)$_6$.

Crosslinking of ligTRE(s)$_6$ to CREB

Weak associations of DNA with protein can be detected more sensitively by crosslinking with platinum than by gel shift binding assays. Gel electrophoresis indicates that the binding of TRE sequences to CREB is about one tenth as extensive as the binding of the CRE sequence [Maekawa et al., EMBO J. Vol. 8:2023-2028 (1989)]. Detection of the association of TRE to CREB is simplified by crosslinking with $K_2PtCl_4$. Gel shift assays on a 6% non-denaturing gel can be used to determine the binding of $[^{32}P]ligCRE(s)_6$, $[^{32}P]ligTRE(s)_6$, and $[^{32}P]ligSp1(s)_6$ to CREB. LigCRE(s)$_6$ is bound ~10 times more efficiently than ligTRE(s)$_6$.

When the same complexes are crosslinked with $K_2PtCl_4$, $[^{32}P]ligTRE(s)_6$ is crosslinked to CREB with ~40% of the efficiency with which $[^{32}P]ligCREB(s)_6$ is crosslinked to CREB. A survey of the results of several experiments shows that the number of pmoles of ligTRE(s)$_6$ that crosslinked to CREB was 3–5-fold higher than the number of pmoles that were detected by gel-shift assays. No bands corresponding to crosslinked products could be seen when it was attempted to crosslink the $[^{32}P]ligSp1(s)_6$, a sequence that does not bind CREB (see SEQ ID NO: 5). This indicates that the crosslinking of ligTRE(s)$_6$ to CREB is sequence specific.

Crosslinking of $[^{32}P]$-ligCRE(s)$_6$ and $[^{32}P]$-LigTRE(s)$_6$ to proteins in a PC12 nuclear cell extract When $[^{32}P]ligCRE(s)_6$ or $[^{32}P]ligTRE(s)_6$ were added to a nuclear cell extract from PC12 cells and treated with $K_2PtCl_4$, they were crosslinked to proteins in the extract. In the case of $[^{32}P]ligTRE(s)_6$, several bands were present on an SDS gel. The major band, as anticipated, had the same mobility as the adduct formed by $[^{32}P]ligTRE(s)_6$ with pure JUN. However, in the case of $[^{32}P]ligCRE(s)_6$, the major band did not have the same mobility as the $[^{32}P]ligCRE(s)_6$CREB adduct. Instead it co-electrophoresed with the ligTRE(s)$_6$-JUN product.

It is believed that in a crude nuclear cell extract, ligCRE(s)$_6$ crosslinks preferentially to the AP-1 binding proteins (FOS, JUN, etc.) to which the CRE sequence is already known to bind [Sassone-Corsi et al., Oncogene Vol. 5:427–431 (1990). Standard gel shift assays using PC12 cell nuclear extracts confirm that the CRE sequence binds more extensively to AP-1 proteins than to the CREB protein.

The invention has been described in detail with particular reference to certain preferred embodiments thereof, but it will be understood that variations and modifications can be effected within the spirit and scope of that which is described and claimed herein.

That which is claimed is:

1. An oligonucleotide for modulating transcription activation of trans-acting factor responsive genes, said oligonucleotide comprising, reading from the 5'-end of said oligonucleotide a first segment, a second segment and a third segment, wherein:

(i) said first segment comprises a sequence of deoxynucleotide or nucleotide residues, said sequence comprising a first core recognition sequence having flanking bases on either side; wherein said first segment, when hybridized with the third segment, forms at least one transcription control recognition sequence of at least 6 nucleotides, (ii) said second segment comprises a sequence of deoxynucleotide or nucleotide residues, said sequence having a length sufficient to allow the formation of a first loop structure between the 3'-end of said first segment and the 5'-end of the third segment, and (iii) said third segment comprises a sequence of deoxynucleotide or nucleotide residues, said sequence comprising a second core recognition sequence having flanking bases on either side, and wherein said second core recognition sequence is complementary to said first core recognition sequence.

2. An oligonucleotide according to claim 1, further comprising a fourth segment, wherein said fourth segment comprises a sequence of deoxynucleotide or nucleotide residues, sufficient to allow the formation of a second loop structure between said first segment and said third segment, wherein said second loop structure is formed by connecting the 5'-end of said first segment to the 3'-end of said fourth segment and the 5'-end of said fourth segment to the 3'-end of said third segment.

3. An oligonucleotide according to claim 2 wherein there is a break in the oligonucleotide backbone of either the first or third segment thereof.

4. An oligonucleotide according to claim 3 wherein the oligonucleotide is dephosphorylated at the 5'-end of the break in either the first or third segment.

5. An oligonucleotide according to claim 4 wherein, in addition to being dephosphorylated, there is deleted from said oligonucleotide, at the site of the break, one or more of said deoxynucleotide or nucleotide residues.

6. An oligonucleotide according to claim 1 wherein said first and third segments are additionally attached to one another by covalent means of attachment.

7. An oligonucleotide according to claim 6 wherein said covalent bonds serve to attach the 5'-end of said first segment to the 3'-end of said third segment.

8. An oligonucleotide according to claim 6 wherein said covalent means of attachment is selected from:

a (poly)alkylene bridge, an $\alpha,\omega$-poly(alkylene) dicarboxylic acid, a binuclear $Pt^{II}$ complex selected from:

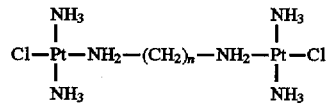

wherein n is 4, 5, or 6; or the result of contacting said oligonucleotide with, psoralen, and then photo-cross-linking by exposure to ultraviolet light.

9. An oligonucleotide according to claim 1 wherein said sequence of deoxynucleotide or nucleotide residues, sufficient to form a loop structure comprises at least 3 residues.

10. An oligonucleotide according to claim 1 wherein said oligonucleotide is further modified so as to be capable of forming a covalent bond with a protein which associates with said transcription control recognition sequence.

11. A composition for modulating transcription activation of trans-acting factor responsive genes, said composition comprising a double-stranded DNA fragment, wherein said DNA fragment contains at least one transcription control recognition sequence of at least 6 nucleotide base pairs, and wherein one strand of said DNA fragment is attached to the other strand by means of at least one linker covalently bound to each strand wherein said linker is selected from:

a sequence of bases sufficient to allow the formation of a loop structure between the 3'-end of one strand of said double-stranded DNA fragment and the 5'-end of the strand complementary thereto, or a sequence of bases sufficient to allow the formation of a loop structure between the 5'-end of one strand of said double-stranded DNA fragment and the 3'-end of the strand complementary thereto, or two sequences of bases sufficient to allow the formation of a loop structure between:

the 3'-end of the first strand of said double-stranded DNA fragment and the 5'-end of the strand complementary thereto and the 3'-end of the complementary strand of said double-stranded DNA fragment, and the 5'-end of the first strand of said double-stranded DNA fragment.

12. A composition according to claim 11 wherein one strand of said DNA fragment is additionally covalently bound to the other strand by a covalent linker selected from:

a (poly)alkylene bridge, an α,ω-poly(alkylene) dicarboxylic acid, a binuclear $Pt^{II}$ complex selected from:

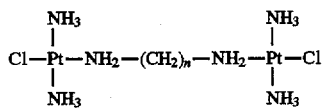

wherein n is 4, 5, or 6; or the result of contacting said oligonucleotide with psoralen, and then photo-cross-linking by exposure to ultraviolet light.

13. A composition according to claim 11 wherein said sequence of bases sufficient to allow the formation of loop structure(s) comprises in the range of about 3 up to 10 nucleotides.

14. A composition according to claim 13 wherein said sequence of bases sufficient to allow the formation of loop structure(s) comprises a sequence of any five nucleotide bases.

15. A method to modulate the transcription of products which are subject to regulation by transcription control recognition sequences, said method comprising administering a therapeutically effective amount of the composition of claim 1 to a subject.

16. A method to modulate the transcription of products which are subject to regulation by transcription control recognition sequences, said method comprising administering a therapeutically effective amount of the composition of claim 11 to a subject.

17. A method to improve the stability of a double-stranded DNA fragment, wherein said DNA fragment contains at least one transcription control recognition sequence of at least 6 nucleotide base pairs, said method comprising introducing at least one linker between the first strand and the strand complementary thereto, wherein said linker is covalently bound to each strand of said double-stranded DNA fragment; and wherein said linker is selected from:

a sequence of bases sufficient to allow the formation of a loop structure between the 3'-end of one strand of said double-stranded DNA fragment and the 5'-end of the strand complementary thereto, or a sequence of bases sufficient to allow the formation of a loop structure between the 5'-end of one strand of said double-stranded DNA fragment and the 3'-end of the strand complementary thereto, or two sequences of bases sufficient to allow the formation of a loop structure between:

the 3'-end of the first strand of said double-stranded DNA fragment and the 5'-end of the strand complementary thereto and the 3'-end of the complementary strand of said double-stranded DNA fragment, and the 5'-end of the first strand of said double-stranded DNA fragment.

18. A method to crosslink oligonucleotides to polypeptides bound thereto, said method comprising incorporating at least one phosphorothioate group into said oligonucleotide and contacting the polypeptide-bound, phosphorothioate containing oligonucleotide with a transition metal catalyst.

19. A method according to claim 18 wherein said transition metal catalyst is $K_2PtCl_4$.

20. A method according to claim 18 wherein said oligonucleotide contains at least four or more phosphorothioate diester linkages incorporated into the recognition sequence of the oligonucleotide.

* * * * *